US010184863B2

(12) United States Patent
Shin

(10) Patent No.: US 10,184,863 B2
(45) Date of Patent: Jan. 22, 2019

(54) TUBERCULAR BACILLUS SLIDE STAINING APPARATUS

(71) Applicant: KOREA STANDARD CO., LTD, Goyang-si (KR)

(72) Inventor: Ji Hyun Shin, Goyang-si (KR)

(73) Assignee: KOREA STANDARD CO., LTD, Goyang-si (KR)

(*) Notice: Subject to any disclaimer, the term of this patent is extended or adjusted under 35 U.S.C. 154(b) by 4 days.

(21) Appl. No.: 15/544,920

(22) PCT Filed: May 13, 2015

(86) PCT No.: PCT/KR2015/004772
§ 371 (c)(1),
(2) Date: Jul. 20, 2017

(87) PCT Pub. No.: WO2016/117767
PCT Pub. Date: Jul. 28, 2016

(65) Prior Publication Data
US 2018/0202905 A1 Jul. 19, 2018

(30) Foreign Application Priority Data
Jan. 22, 2015 (KR) ........................ 10-2015-0010864

(51) Int. Cl.
*G01N 1/00* (2006.01)
*G01N 1/31* (2006.01)
*G01N 21/29* (2006.01)
*G01N 21/78* (2006.01)
*G01N 33/483* (2006.01)

(52) U.S. Cl.
CPC ............... *G01N 1/312* (2013.01); *G01N 1/31* (2013.01); *G01N 21/29* (2013.01); *G01N 21/78* (2013.01); *G01N 33/483* (2013.01); *G01N 2001/317* (2013.01)

(58) Field of Classification Search
CPC ........................................................ G01N 1/00
See application file for complete search history.

(56) References Cited

U.S. PATENT DOCUMENTS 6,858,432 B2 * 2/2005 Stokes ..................... G01N 1/30
252/408.1

FOREIGN PATENT DOCUMENTS

| | | |
|---|---|---|
| JP | 2002-071538 | 3/2002 |
| KR | 10-0743225 | 7/2007 |
| KR | 10-1087303 | 11/2011 |
| KR | 10-1416966 | 7/2014 |

* cited by examiner

*Primary Examiner* — Jyoti Nagpaul
(74) *Attorney, Agent, or Firm* — Lex IP Meister, PLLC

(57) ABSTRACT

The present invention relates to an apparatus for staining a *Mycobacterium tuberculosis* slide, which enables a sample on a slide plate to be rapidly and uniformly heated and prevents a dye solution and a washing solution, supplied to a rotatable staining plate, from remaining the rotatable staining plate, thus clear differential staining and maintaining the rotatable staining plate clean. Specifically, the apparatus for staining the *Mycobacterium tuberculosis* slide according to the present invention comprises: a hot-air supply unit disposed above a staining unit and configured such that circulating hot air is laterally discharged from the hot-air supply unit; and a slanted groove for centrifugal discharge, formed at the outer edge of the slide mounting groove of the rotatable staining plate.

4 Claims, 6 Drawing Sheets

【Figure 1】
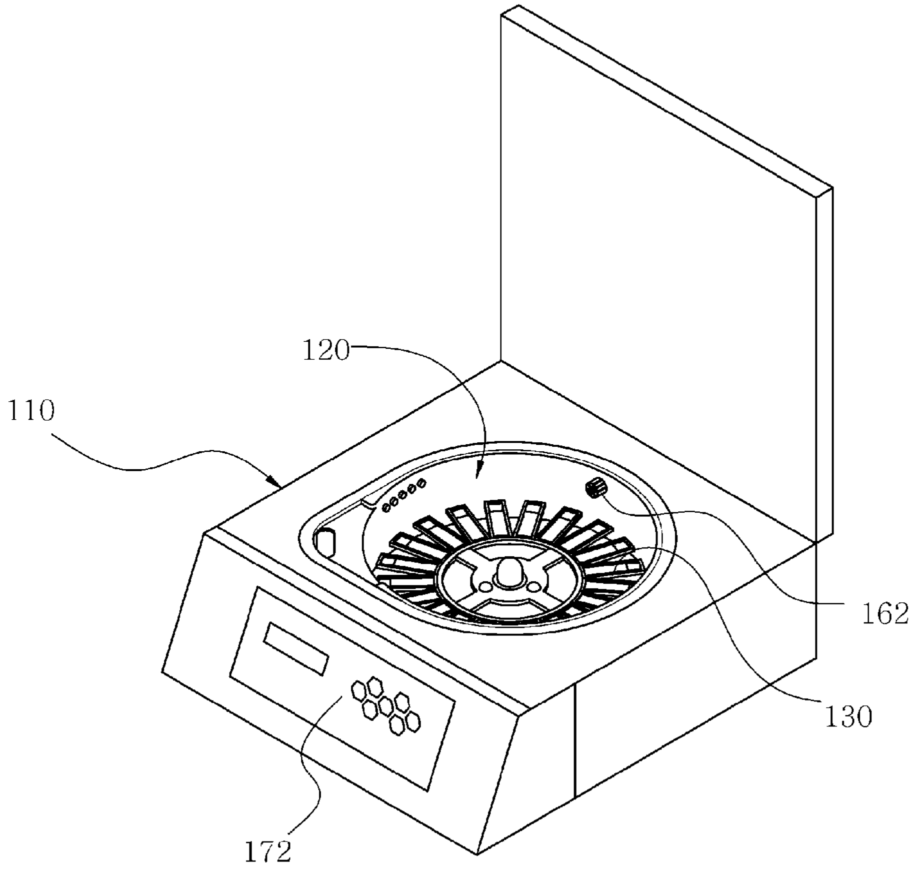

【Figure 2】
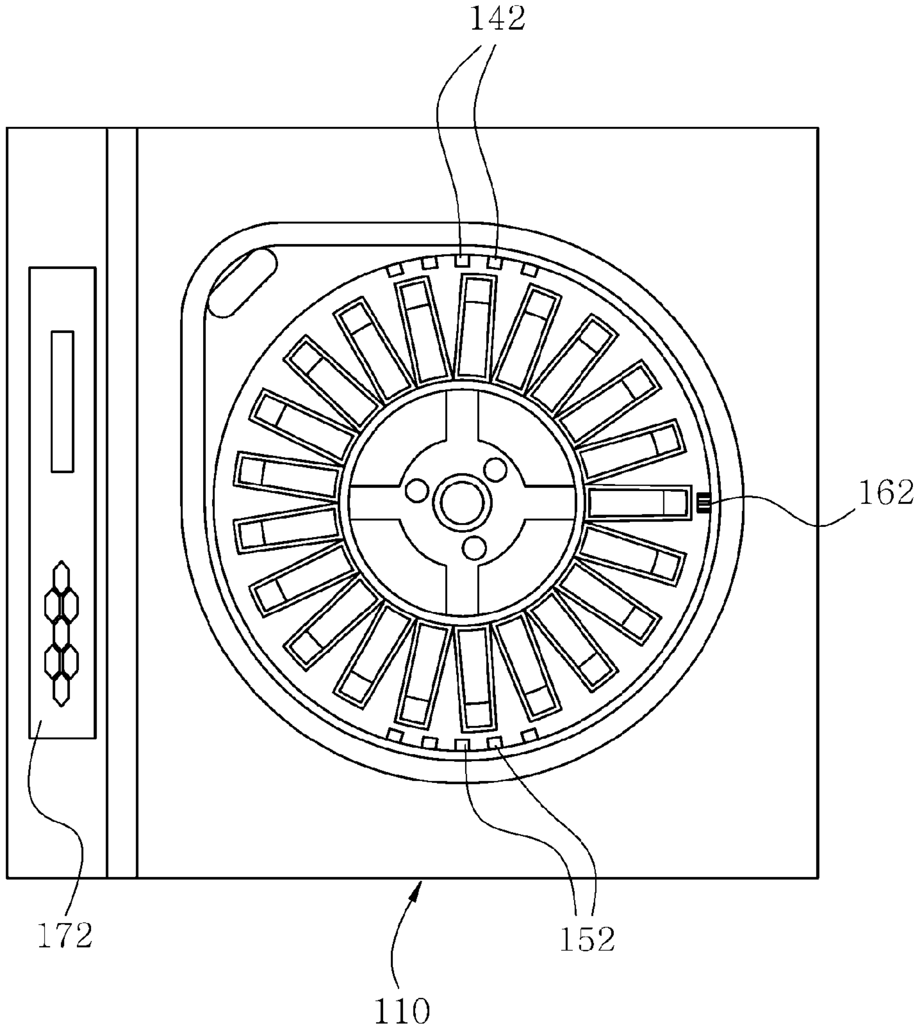

【Figure 3】
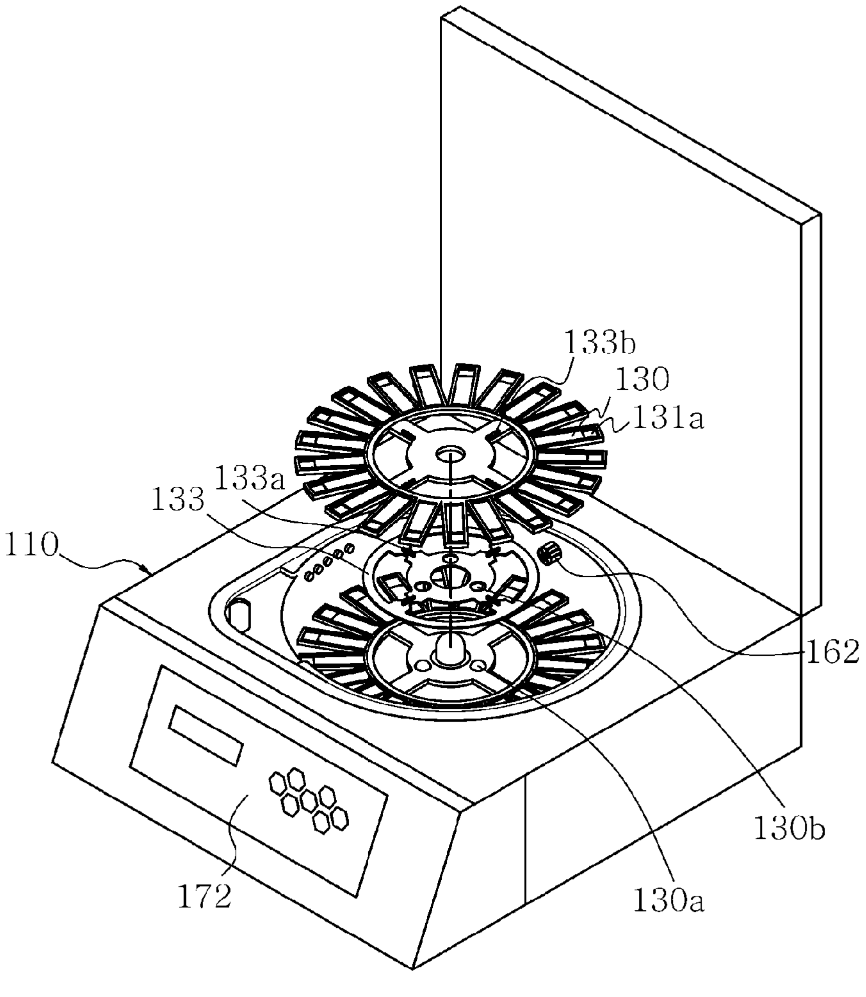

【Figure 4】
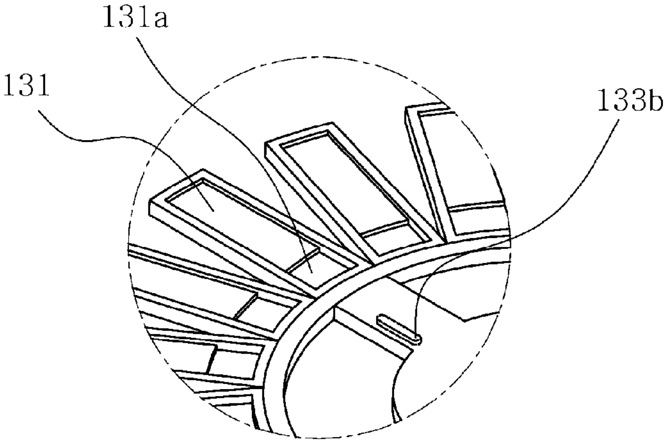
【Figure 5】
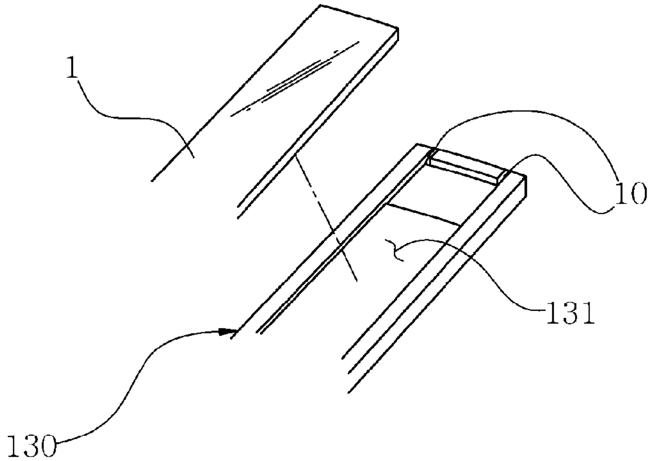

【Figure 6】
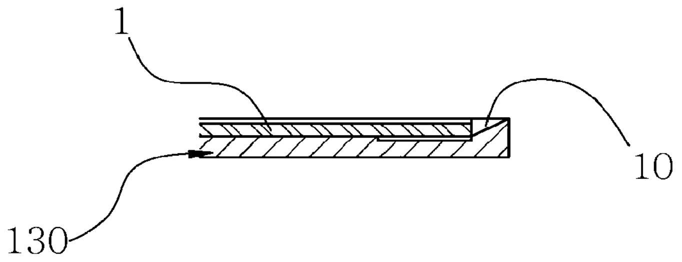
【Figure 7】
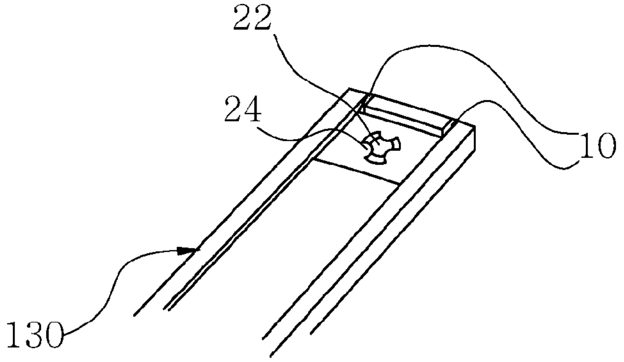

【Figure 8】
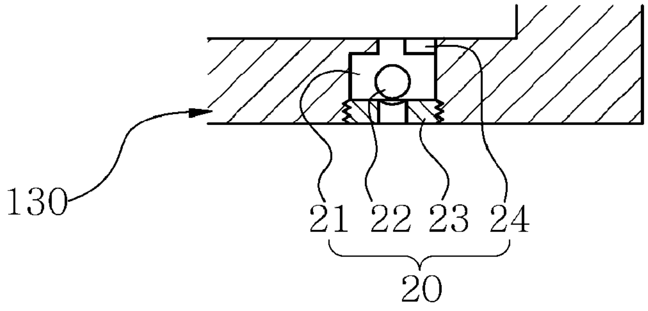
【Figure 9】
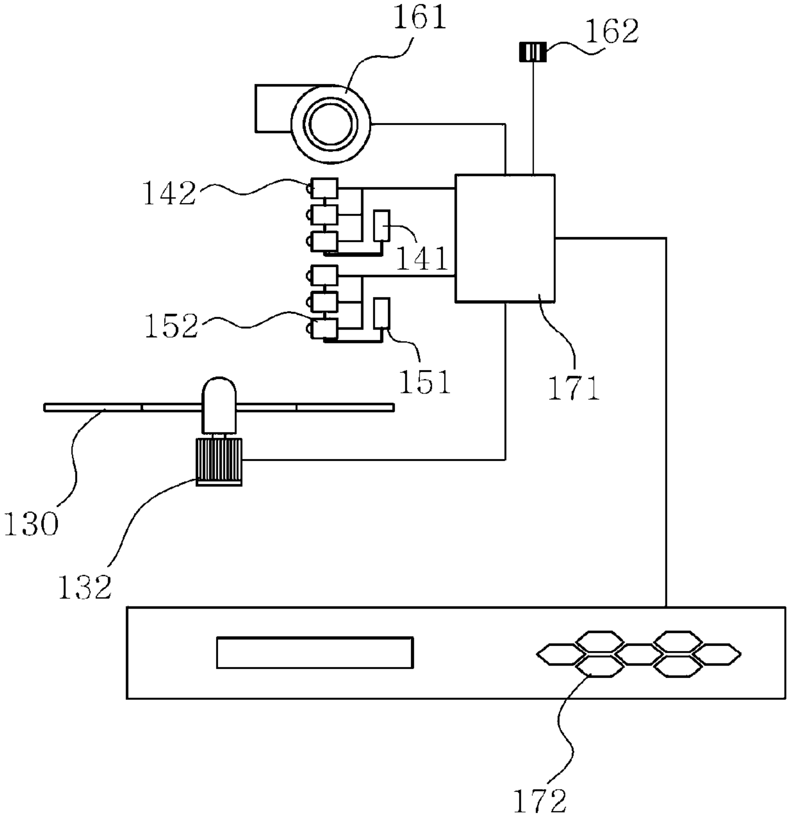

TUBERCULAR BACILLUS SLIDE STAINING APPARATUS

TECHNICAL FIELD

The present invention relates to an apparatus for staining a *Mycobacterium tuberculosis* slide. More specifically, an object of the present invention is to provide an apparatus for staining a *Mycobacterium tuberculosis* slide, comprising a hot-air supply unit disposed above a staining unit and configured such that circulating hot air is laterally discharged from the hot-air discharge unit, the apparatus having a slanted groove for centrifugal discharge formed at the outer edge of the slide mounting groove of a rotatable staining plate, so that a sample applied to a slide plate will be rapidly and uniformly heated and a dye solution and washing solution applied to the rotatable staining plate will not remain, thereby achieving clear differential staining and maintaining the rotatable staining plate clean.

Another object of the present invention is to provide an apparatus for staining a *Mycobacterium tuberculosis* slide, comprising a plurality of rotatable staining plates so as to enable a plurality of slide plates to be stained at the same time.

BACKGROUND ART

Generally, an apparatus for staining a *Mycobacterium tuberculosis* slide is configured such that *Mycobacterium tuberculosis* can be visually detected by acid-fast staining of the slide having applied thereto a sample collected from a patient.

As disclosed in Korean Patent No. 1416966, this device for staining the *Mycobacterium tuberculosis* slide comprises: a staining unit provided in a staining apparatus body; a rotatable staining plate provided in the staining unit so as to be rotated by a motor; a staining nozzle disposed on the inner wall of the staining unit and configured to supply a dye solution to a slide disposed on the rotatable staining plate; a washing nozzle configured to supply a washing solution to the slide; a staining plate heater configured to heat the rotatable staining plate; a controller configured to control staining of a sample; and a staining operating unit enabling a user to input an operating signal into the controller.

The conventional apparatus for staining the *Mycobacterium tuberculosis* slide as described above is configured such that when the slide having the sample applied thereto is disposed on the rotatable staining plate and stained by operating the operating unit, the controller operates the staining heater provided in the rotatable staining plate to heat the slide to a certain temperature.

To the slide on which the sample had been heated as described above, a dye solution is applied through the staining nozzle to stain the slide. After completion of the staining, a washing solution is sprayed onto the slide.

However, the rotatable staining plate in the conventional apparatus for staining the *Mycobacterium tuberculosis* slide as described above is configured such that the staining heater provided on the rotatable staining plate heats the sample by heat conduction through the slide. Thus, the conventional apparatus has problems in that heating of the sample is time-consuming and the sample is dried and is not uniformly heated.

In addition, the conventional apparatus for staining the *Mycobacterium tuberculosis* slide has problems in that the dye solution remains in a slide mounting groove formed in the rotatable staining plate, is not clearly removed from the groove, and is mixed with a dye solution supplied, making clear staining impossible or causing contamination of the rotatable staining plate.

DISCLOSURE

Technical Problem

Accordingly, the present invention has been made in order to solve the problems of the conventional apparatus for staining the *Mycobacterium tuberculosis* slide as described above. The problems of the conventional apparatus are as follows. The rotatable staining plate in the conventional apparatus for staining the *Mycobacterium tuberculosis* slide is configured such that the staining heater provided on the rotatable staining plate heats the sample by heat conduction through the slide. Thus, heating of the sample is time-consuming and the sample is dried and is not uniformly heated. A dye solution remains in a slide mounting groove formed in the rotatable staining plate, is not clearly removed from the groove, and is mixed with a dye solution supplied, making clear staining impossible or causing contamination of the rotatable staining plate.

Technical Solution

The present invention provides an apparatus for staining a *Mycobacterium tuberculosis* slide, comprising: a hot-air supply unit disposed above a staining unit and configured such that circulating hot air is laterally discharged from the hot-air supply unit; and a centrifugal discharge slanted groove formed at the outer edge of the slide mounting groove of a rotatable staining plate.

The present invention also provides an apparatus for staining a *Mycobacterium tuberculosis* slide, comprising a plurality of rotatable staining plates.

Advantageous Effects

The apparatus for staining the staining *Mycobacterium tuberculosis* slide according to the present invention comprises a hot-air supply unit disposed above a staining unit and configured such that circulating hot air is laterally discharged from the hot-air supply unit. Thus, a sample applied to a slide plate is uniformly heated from the top of a staining unit by convection movement, and thus the sample is uniformly and clearly heated without being dried. Furthermore, a slanted groove for centrifugal discharge is formed at the outer edge of the slide mounting plate of a rotatable staining plate. Thus, a dye solution and washing solution supplied to the rotatable staining plate is clearly centrifuged without remaining on the rotatable staining plate during centrifugal rotation of the rotatable staining plate, and thus the sample is clearly differentially stained in each step and the rotatable staining plate is maintained clean.

In addition, the apparatus according to the present invention may comprise a plurality of rotatable staining plates so that samples applied to a plurality of slide plates can be stained at the same time.

DESCRIPTION OF DRAWINGS

FIG. 1 is a view illustrating one embodiment of the present invention.

FIG. 2 is a top view illustrating one embodiment of the present invention.

FIG. 3 is a view illustrating one embodiment of the present invention in which a plurality of rotatable staining plates are disposed.

FIG. 4 is a view illustrating one embodiment of the present invention in which a taking-out pressing groove is provided at the inner end of a slide mounting groove according to one embodiment of the present invention.

FIG. 5 is a detailed view illustrating a rotatable staining plate according to one embodiment of the present invention.

FIG. 6 is a detailed view illustrating the side cross-section of the rotatable staining plate shown in FIG. 5.

FIG. 7 is a detailed view illustrating a rotatable staining plate according to another embodiment of the present invention.

FIG. 8 is a detailed view illustrating the side cross-section of the rotatable staining plate shown in FIG. 7.

FIG. 9 is a view illustrating major elements according to the present invention.

BEST MODE

Hereinafter, the present invention will be described in detail with reference to the accompanying drawings.

The staining apparatus according to the present invention is configured such that a sample applied to a slide plate is uniformly and clearly heated and a dye solution and washing solution supplied to the slide plate are clearly separated and removed from a rotatable staining plate.

Specifically, the present invention provides an apparatus for staining a *Mycobacterium tuberculosis* slide, comprising: a staining apparatus body 110 having a cylindrical staining unit 120 therein and configured such that the top of the staining unit 120 is opened or closed by a plate-like cover; a rotatable staining plate 130 disposed in the central portion of the staining unit 120 so as to be rotated by a motor 132 provided in the staining apparatus body 110; a staining nozzle 142 disposed on the inner wall of the staining unit 120 and configured to spray a dye solution, pumped by a dye solution pump 141, onto a slide plate 1 mounted in each of slide mounting grooves 131 of the rotatable staining plate 130; a washing nozzle 152 configured to spray a washing solution, pumped by a washing solution pump 151, onto the slide plate 1 mounted in the slide mounting groove 131; a hot-air supply unit 161 disposed above the staining unit 120 and configured such that circulating hot air is laterally discharged from the hot-air supply unit 161 so that a sample applied to the slide plate 1 mounted in the slide mounting groove 131 of the rotatable staining plate 130 can be heated by air conduction above the staining unit 120; a staining unit temperature sensor 162 configured to sense the temperature of the staining unit 120 heated by hot air supplied from the hot-air supply unit 161 to the inner wall of the staining unit 120; a controller 171 configured to control operation of a motor 132, a pump and the hot-air supply unit 161; and a staining operation unit 172 provided outside the staining apparatus body 110 and configured to enable a user to input an operating signal into the controller 171.

Meanwhile, in the practice of the present invention, the rotatable staining plate 130 may comprise a plurality of rotatable staining plates stacked on each other by a stacking unit.

The stacking unit comprises a spacing stacking unit 133 configured such that an upper rotatable staining plate 130 is stacked above a lower rotatable staining plate 130 in such a manner that the slide mounting grooves 131 of the upper rotatable staining plate 130 alternate with the slide mounting grooves 131 of the lower rotatable staining plate 130. On the upper surface of the spacing stacking unit 133, a coupling protrusion **133*b* is formed which is coupled to a coupling groove 133*a* formed on the lower surface of the upper rotatable staining plate 130**.

Meanwhile, the spacing stacking unit 133 is configured such that it is separable from the rotatable staining plate 130 and such that it supports the slide 1 mounted such that the outer end thereof is beyond the inner end of the spacing stacking unit 133, thereby preventing the mounted slide 1 from being taken out.

The spacing stacking unit 133 has two or more staining plate coupling grooves **130*b* formed thereon, which are coupled to two or more staining plate protrusions 130*a* protruding from the rotatable staining plate 130**.

Furthermore, a taking-out pressing groove **131*a* is formed so that when one end of the slide plate 1 mounted in any one of the inner and outer ends of the slide mounting groove 131 of the rotatable staining plate 130 is pressed down, one end of the pressed slide plate 1** will be moved downward while the other end will be moved upward so that the slide plate can be easily taken out.

Furthermore, at the outer edge of the slide mounting groove 131 of the rotatable staining plate 130, a slanted groove 10 for centrifugal discharge is formed to be slanted upward so that the remaining dye solution or washing solution supplied during staining or washing can be discharged from the slide mounting groove 131, so that negative pressure will not act on the stained state of a sample applied to the slide plate 1.

Furthermore, in the practice of the present invention, at the bottom of the outer edge of the slide mounting groove 131 of the rotatable staining plate, a buoyancy valve 20 may be provided which is configured such that when the dye solution or the washing solution excessively remains, buoyancy is applied, and when the dye solution or the washing solution does not remain, buoyancy does not act on the slide plate 1.

The buoyancy valve 20 comprises: a valve chamber 21 formed by perforating the bottom of the slide mounting groove 131; a buoyancy body 22 received in the valve chamber 21; a valve cap 23 provided beneath the valve chamber 21 so as to prevent the buoyancy body 22 from being removed downward and form a valve sheet; and a stepped valve portion 24 formed so as to prevent the buoyancy body 22 from being removed upward from the valve chamber 21.

Hereinafter, a process of using the apparatus for staining the *Mycobacterium tuberculosis* slide according to the present invention will be described.

As described above, the apparatus for staining the *Mycobacterium tuberculosis* slide according to the present invention comprises a hot-air supply unit 161 disposed above the staining unit 120 and configured such that circulating hot air is laterally discharged from the hot-air supply unit 161 so that a sample applied to the slide plate 1 mounted in the slide mounting groove 131 of the rotatable staining plate 130 can be heated by air conduction above the staining unit 120. When this staining apparatus is applied, the sample applied to the slide plate 1 is not heated by heat conduction through the rotatable staining plate 130, but is heated by air conduction from the staining unit 120 heated from the top as a result of convection flow of air. Thus, the sample is uniformly and steadily heated in a state in which drying of the sample is minimized.

Furthermore, when the rotatable staining plate 130 composed of a plurality of rotatable staining plates stacked on each other by the stacking unit is used in the practice of the present invention, the slide plate 1 mounted in the plurality of rotatable staining plates 130 can be stained in one staining process.

Moreover, when the staining apparatus comprises the spacing stacking unit 133 through which the rotatable staining plates 130 are coupled to each other by the coupling protrusion 133*b* and the coupling groove 133*a*, it is ensured that the slide mounting grooves 131 of the upper rotatable staining plate 130 alternate with the slide mounting grooves 131 of the lower rotatable staining plate 130.

Furthermore, when the taking-out pressing groove 131*a* is formed at any one of the outer end and inner end of the slide mounting groove 131 of the rotatable staining plate 130, the slide plate 1 mounted in the slide mounting groove 131 can be easily taken out.

In addition, when the slanted groove 10 for centrifugal discharge is formed at the outer edge of the slide mounting groove 131 of the rotatable staining plate 130 according to the present invention, the remaining dye solution or washing solution supplied during staining or washing is centrifugally discharged through the slanted groove 10 during rotation of the rotatable staining plate 130.

During discharge of the staining solution or washing solution remaining the slide mounting groove 131, a centrifugal force acts on the slanted groove 10, and thus is prevented from acting on the sample applied to the slide plate 1.

In addition, if the buoyancy valve 20 is provided at the bottom of the outer edge of the slide mounting groove 131 of the rotatable staining plate 130 according to the present invention, when the staining solution or the washing solution excessively remains in the slide mounting groove 131, the buoyancy body 22 of the buoyancy valve 20 moves upward by buoyancy to open the valve so that the dye solution or the washing solution will be rapidly discharged through the buoyancy valve 20. When discharge of the dye solution or the washing solution is completed, the buoyancy valve 20 is closed, thus preventing buoyancy from acting on the sample applied to the slide plate 1 during rotation of the rotatable staining plate 130.

The invention claimed is:

1. An apparatus for staining a *Mycobacterium tuberculosis* slide, comprising:

a staining apparatus body 110 having a cylindrical staining unit 120 therein and configured such that a top of the staining unit 120 is opened or closed by a plate-like cover;

a rotatable staining plate 130 disposed in a central portion of the staining unit 120 so as to be rotated by a motor 132 provided in the staining apparatus body 110;

a staining nozzle 142 disposed on an inner wall of the staining unit 120 and configured to spray a dye solution, pumped by a dye solution pump 141, onto a slide plate 1 mounted in each of slide mounting grooves 131 of the rotatable staining plate 130;

a washing nozzle 152 configured to spray a washing solution, pumped by a washing solution pump 151, onto the slide plate 1 mounted in the slide mounting groove 131;

a hot-air supply unit 161 disposed above the staining unit 120 and configured such that circulating hot air is laterally discharged from the hot-air supply unit 161 so that a sample applied to the slide plate 1 mounted in the slide mounting groove 131 of the rotatable staining plate 130 is heated by air conduction above the staining unit 120;

a staining unit temperature sensor 162 configured to sense the temperature of the staining unit 120 heated by hot air supplied from the hot-air supply unit 161 to the inner wall of the staining unit 120;

a controller 171 configured to control operation of the motor 132, the pumps and the hot-air supply unit 161; and a staining operation unit 172 provided outside the staining apparatus body 110 and configured to enable a user to input an operating signal into the controller 171, wherein a taking-out pressing groove 131*a* is formed at any one of outer and inner ends of the slide mounting grooves 131 of the rotatable staining plate 130, such that when one end of the mounted slide plate 1 is pressed down, one end of the pressed slide plate 1 moves downward while the other end moves upward so that the slide plate 1 is easily taken out.

2. The apparatus of claim 1, comprising a plurality of the rotatable staining plates 130 stacked on each other by a stacking unit, wherein the stacking unit comprises a spacing stacking unit 133 configured such that an upper rotatable staining plate 130 is stacked above a lower rotatable staining plate 130 in such a manner that the slide mounting grooves 131 of the upper rotatable staining plate 130 alternate with the slide mounting grooves 131 of the lower rotatable staining plate 130, and the upper surface of the spacing stacking unit 133 has formed thereon a coupling protrusion 133*b* which is coupled to a coupling groove 133*a* formed on the lower surface of the upper rotatable staining plate 130.

3. The apparatus of claim 1, wherein the spacing stacking unit 133 is configured such that it is separable from the rotatable staining plate 130 and such that it supports the slide 1 mounted such that the outer end thereof is beyond the inner end of the spacing stacking unit 133, thereby preventing the mounted slide 1 from being taken out, and the spacing stacking unit 133 has two or more staining plate coupling grooves 130*b* formed thereon, which are coupled to two or more staining plate protrusions 130*a* protruding from the rotatable staining plate 130.

4. The apparatus of claim 1, wherein a slanted groove 10 for centrifugal discharge is formed to be slanted upward at the outer edge of the slide mounting groove 131 of the rotatable staining plate 130, so that the remaining dye solution or washing solution supplied during staining or washing is discharged from the slide mounting groove 131, so that negative pressure does not act on a stained state of a sample applied to the slide plate 1; and a bottom of the outer edge of the slide mounting groove 131 of the rotatable staining plate has a buoyancy valve 20 which is configured such that when the dye solution or the washing solution excessively remains, buoyancy is applied, and when the dye solution or the washing solution does not remain, buoyancy does not act on the slide plate 1, wherein the buoyancy valve 20 comprises: a valve chamber 21 formed by perforating the bottom of the slide mounting groove 131; a buoyancy body 22 received in the valve chamber 21; a valve cap 23 provided beneath the valve chamber 21 so as to prevent the buoyancy body 22 from being removed downward and form a valve sheet; and a stepped valve portion 24 formed so as to prevent the buoyancy body 22 from being removed upward from the valve chamber 21.

* * * * *